(12) United States Patent
Okihara et al.

(10) Patent No.: US 11,819,665 B2
(45) Date of Patent: Nov. 21, 2023

(54) PREFILLED SYRINGE, SYRINGE ASSEMBLY, METHOD FOR MANUFACTURING PREFILLED SYRINGE, AND METHOD FOR INCREASING SURFACE AREA

(71) Applicant: TERUMO KABUSHIKI KAISHA, Tokyo (JP)

(72) Inventors: Hitoshi Okihara, Fujinomiya (JP); Fumiya Matsumoto, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 167 days.

(21) Appl. No.: 17/365,316

(22) Filed: Jul. 1, 2021

(65) Prior Publication Data
US 2022/0001108 A1    Jan. 6, 2022

(30) Foreign Application Priority Data
Jul. 1, 2020    (JP) .................................. 2020-114114

(51) Int. Cl.
*A61M 5/31*    (2006.01)
*A61M 5/32*    (2006.01)

(52) U.S. Cl.
CPC ........ *A61M 5/3129* (2013.01); *A61M 5/3202* (2013.01); *A61M 2005/3131* (2013.01); *A61M 2202/064* (2013.01); *A61M 2207/00* (2013.01)

(58) Field of Classification Search
CPC .............. A61M 5/3129; A61M 5/3202; A61M 2005/3131; A61M 2202/064; A61M 2207/00; A61M 2005/3106; A61M 2005/3118; A61M 5/1782; A61J 1/1412; A61J 1/2089; A61J 1/2096
See application file for complete search history.

(56) References Cited

U.S. PATENT DOCUMENTS

| | | | |
|---|---|---|---|
| 6,440,101 B1 * | 8/2002 | Grabenkort | A61M 5/31596 604/82 |
| 2004/0087906 A1 * | 5/2004 | Henderson | A61M 5/345 604/187 |
| 2013/0338575 A1 * | 12/2013 | Glocker | A61M 5/286 604/57 |

FOREIGN PATENT DOCUMENTS

JP     2014508603 A     4/2014

\* cited by examiner

*Primary Examiner* — Brandy S Lee
*Assistant Examiner* — Fatimata Sahra Diop
(74) *Attorney, Agent, or Firm* — BUCHANAN INGERSOLL & ROONEY PC

(57) ABSTRACT

A prefilled syringe includes a barrel body, a gasket that seals a proximal end side of a medicine chamber of the barrel body, and a cap that is attached to a tip and seals a distal end side of the medicine chamber. The cap includes a surface area increasing member that extends to the proximal end side, is inserted into a flow path of the tip, and protrudes to the medicine chamber to increase a surface area of a medicine solidified in a lump in the medicine chamber.

19 Claims, 14 Drawing Sheets

PREFILLED SYRINGE, SYRINGE ASSEMBLY, METHOD FOR MANUFACTURING PREFILLED SYRINGE, AND METHOD FOR INCREASING SURFACE AREA

CROSS-REFERENCES TO RELATED APPLICATIONS

This application claims priority to Japanese Patent Application Serial No. 2020-114114 filed on Jul. 1, 2020, the entire content of which is incorporated herein by reference.

FIELD OF THE DISCLOSURE

The present disclosure relates to a prefilled syringe provided by enclosing a powdery medicine in the prefilled syringe, a syringe assembly, a method for manufacturing a prefilled syringe, and a method for increasing a surface area of a medicine solidified in a lump in a prefilled syringe.

BACKGROUND DISCUSSION

A product in which a medicine is sealed inside a syringe is known as a prefilled syringe. The medicine sealed inside the syringe can be a powdery medicine.

The prefilled syringe in which the powdery medicine is enclosed is subjected to an operation of opening a sealed syringe cap immediately before use and sucking water, for example, distilled water or saline from the distal end portion (syringe tip). The water or saline is used for diluting the powdery medicine and injection of the diluted powdery medicine. As set forth, the powdery medicine is dissolved in the water is then sucked into the syringe, and then a needle tube is attached to the syringe tip and used.

In the prefilled syringe enclosing a powdery medicine, the medicine may be solidified in a lump in the syringe tip during storage. In such a case, a narrow flow path inside the syringe tip can be blocked by a lump of medicine, and the suction of the water for injection can be hindered. Therefore, Japanese Patent Application Publication No. 2014-508603 A discloses a prefilled syringe in which a syringe cap is provided with a protrusion that closes the inside of a syringe tip in order to prevent blockage of a flow path inside the syringe tip.

A lyophilizate obtained by injecting a medicine in a liquid state and then freeze-drying the liquid medicine may be enclosed in the prefilled syringe. Since the lyophilizate is solidified in a lump in the body portion and has a relatively small surface area in contact with the solution taken into the syringe from the syringe tip, it may take time to dissolve the lyophilizate.

In addition, even a powder in the prefilled syringe may be solidified in a lump in the body portion during storage, and it may take time to dissolve the powder.

SUMMARY

A prefilled syringe, a syringe assembly, a method for manufacturing a prefilled syringe, and a method for increasing a surface area are disclosed, which are capable of rather easily dissolving a lyophilizate or a powder solidified in a lump within a prefilled syringe.

In accordance with one aspect, a prefilled syringe is disclosed, which includes: a barrel body including a cylindrical body portion having a medicine chamber in which a medicine is sealed, a shoulder portion formed at a distal end of the body portion and having a reduced diameter of the body portion, and a tip extending from a distal end of the shoulder portion toward a distal end side and having a flow path formed in the tip; a gasket configured to be inserted into the body portion and to seal a proximal end side of the medicine chamber; and a cap configured to be attached to the tip and sealing a distal end side of the medicine chamber. The cap has a surface area increasing member that extends toward a proximal end side and is inserted into the flow path of the tip, and protrudes toward the medicine chamber side to increase a surface area of the medicine solidified in a lump in the medicine chamber.

In accordance with another aspect, a syringe assembly is disclosed, which includes: a barrel body including a cylindrical body portion having a medicine chamber in which a medicine is sealed, a shoulder portion formed at a distal end of the body portion and having a reduced diameter of the body portion in a tapered shape, and a tip extending from a distal end of the shoulder portion toward a distal end side and having a flow path formed in the tip; and a cap attached to the tip and sealing a distal end side of the medicine chamber. The cap has a surface area increasing member that extends toward a proximal end side and is inserted into the flow path of the tip, and protrudes toward the medicine chamber side to increase a surface area of the medicine solidified in a lump in the medicine chamber.

In accordance with a further aspect, a method is disclosed for manufacturing a prefilled syringe as disclosed herein, which includes: causing the surface area increasing member to protrude into the medicine chamber before the medicine in the medicine chamber is solidified in a lump.

In accordance with another aspect, a surface area increasing method is disclosed for increasing a surface area of a medicine solidified in a lump in the medicine chamber using the prefilled syringe disclosed herein, the method including: increasing a surface area of the medicine by relatively moving the surface area increasing member protruding to the medicine chamber with respect to the medicine when removing the cap.

According to the prefilled syringe, the syringe assembly, the method for manufacturing the prefilled syringe, and the method for increasing the surface area, the contact area between the lyophilizate or the powder solidified in a lump and the solution can be increased, and thus the medicine can be rather easily dissolved.

In accordance with a further aspect, a syringe assembly is disclosed comprising: a barrel body including a cylindrical body portion includes a medicine chamber configured to receive a medicine, a shoulder portion formed at a distal end of the body portion and having a reduced diameter of the body portion, and a tip extending from a distal end of the shoulder portion toward a distal end side and having a flow path formed in the tip; a gasket configured to be inserted into the body portion and to seal a proximal end side of the medicine chamber; and a cap configured to be attached to the tip and to seal a distal end side of the medicine chamber, wherein the cap includes a surface area increasing member that extends toward a proximal end side and configured to inserted into the flow path of the tip, and protrudes toward the medicine chamber.

DETAILED DESCRIPTION

Figure 1:
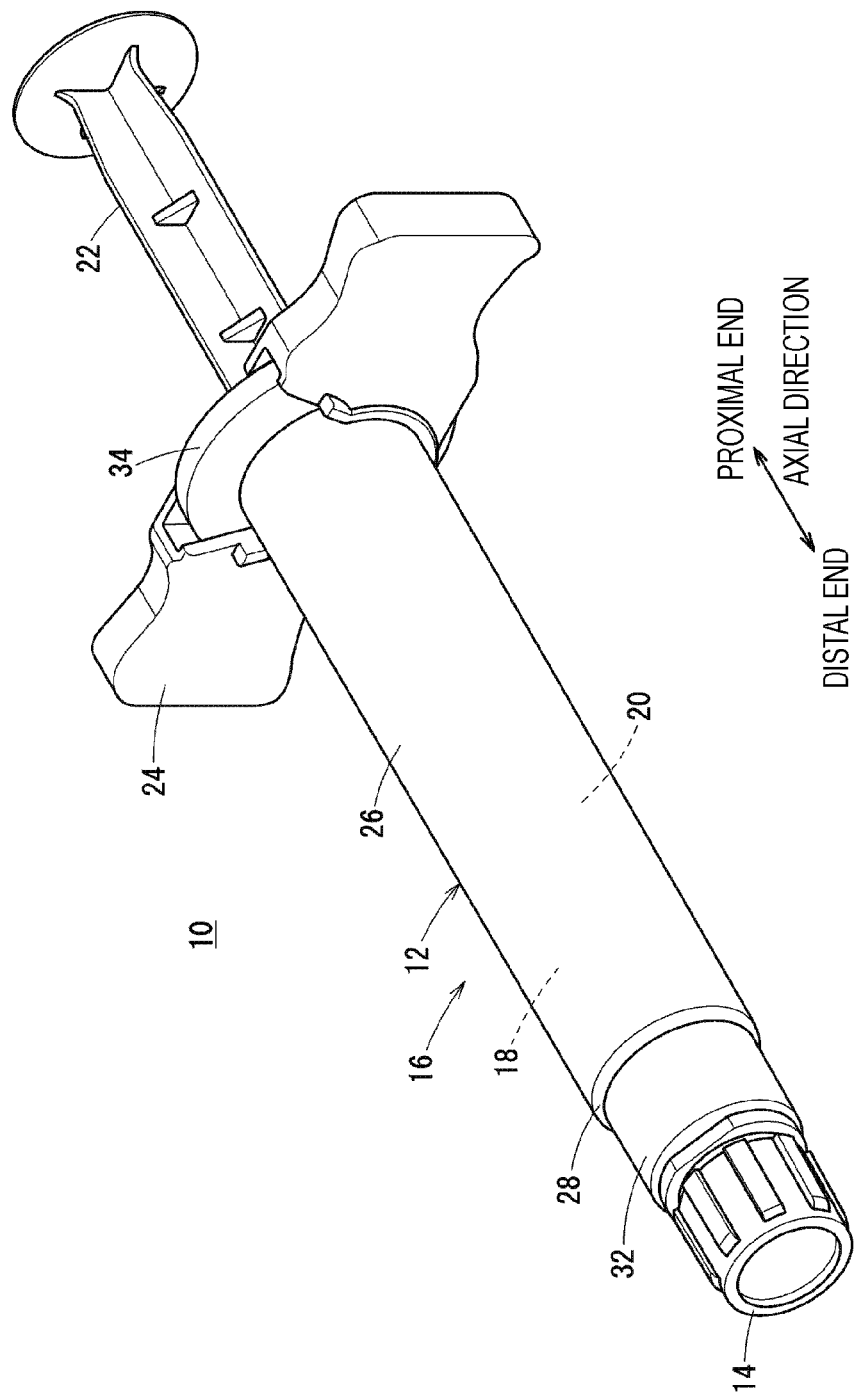
FIG. 1 is a perspective view of a prefilled syringe according to a first exemplary embodiment.

Set forth below with reference to the accompanying drawings is a detailed description of embodiments of a prefilled syringe provided by enclosing a powdery medicine in the prefilled syringe, a syringe assembly, a method for manufacturing a prefilled syringe, and a method for increasing a surface area of a medicine solidified in a lump in a prefilled syringe. Note that since embodiments described below are preferred specific examples of the present disclosure, although various technically preferable limitations are given, the scope of the present disclosure is not limited to the embodiments unless otherwise specified in the following descriptions. In addition, note that dimensional ratios in the drawings may be exaggerated and different from actual ratios for convenience of description. In the following description, a side on which a syringe tip (tip) is formed is referred to as a "distal end side" or a "distal end direction", and a side on which a plunger insertion port of a syringe is formed is referred to as a "proximal end side" or a proximal end direction.

First Exemplary Embodiment

As illustrated in FIG. 1, a prefilled syringe 10 includes a syringe assembly 16 having a barrel body 12 having a medicine chamber 18 in the barrel body 12 and a cap 14, a gasket 20 slidably inserted into the barrel body 12, a plunger 22 connected to the gasket 20, and a grip 24 attached to a proximal end side of the barrel body 12.

Figure 2:
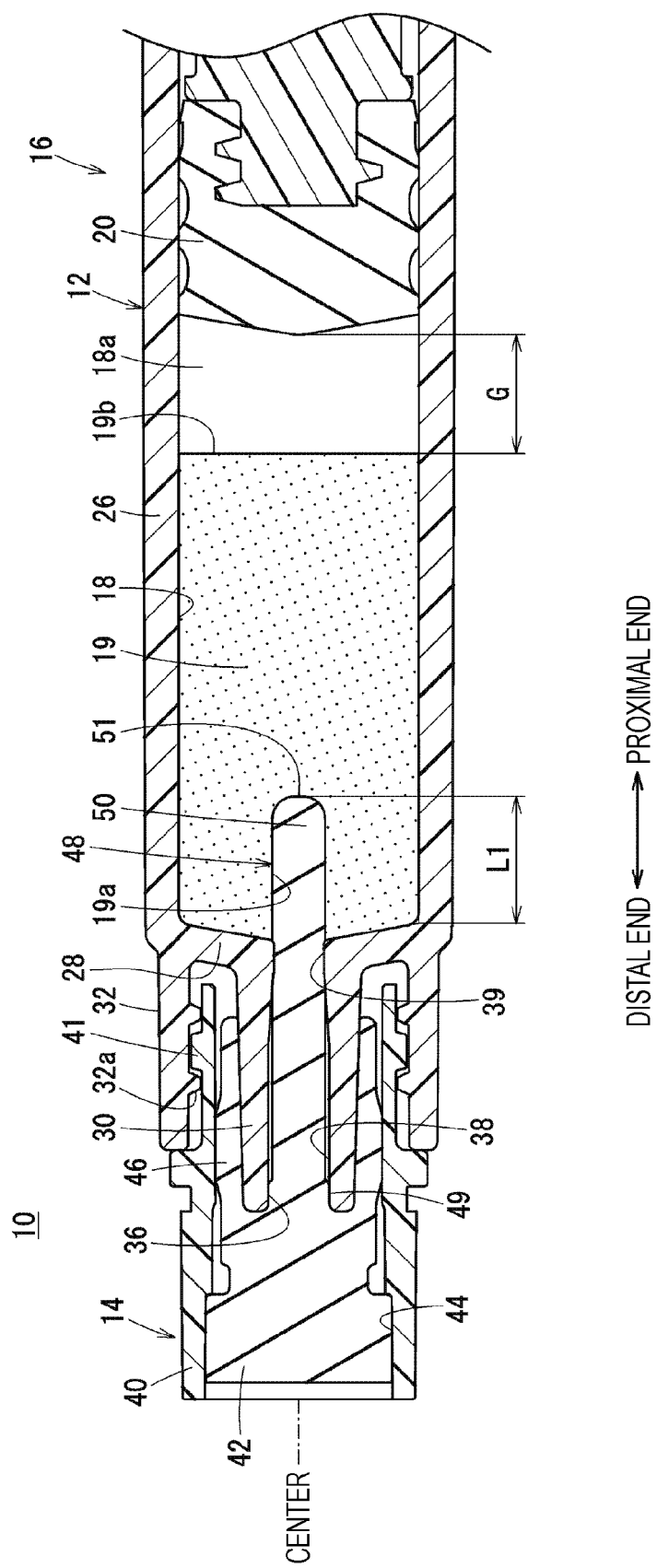
FIG. 2 is a cross-sectional view of the vicinity of a distal end portion of the prefilled syringe of FIG. 1.

As illustrated in FIG. 2, the barrel body 12 includes a hollow body portion 26 having a medicine chamber 18 capable of being filled with a medicine 19. As illustrated in FIG. 2, a shoulder portion 28 in which the body portion 26 is reduced (i.e., decreases) in diameter is provided at the distal end portion of the body portion 26, and a tip 30 (male Luer portion) is provided to protrude in the distal end direction from the distal end portion of the shoulder portion 28. In addition, a Luer lock portion 32 protruding in a cylindrical shape so as to surround the outer peripheral side of the tip 30 is provided from the distal end portion of the body portion 26 of the barrel body 12.

As illustrated in FIG. 1, a flange 34 having a diameter that expands outward is provided at a proximal end portion of the body portion 26. The grip 24 is attached to the flange 34. The body portion 26, the shoulder portion 28, the tip 30, the Luer lock portion 32, and the flange 34 are integrally formed. The material of the barrel body 12 is not particularly limited. For example, the barrel body 12 can be formed of various resin materials, a metal material such as stainless steel, glass, or the like.

The body portion 26 is formed in a cylindrical shape and extends in the axial direction. As illustrated in FIG. 2, the shoulder portion 28 whose diameter is reduced (i.e., outer diameter of the shoulder portion 28 decreases) toward the tip 30 is provided at the distal end portion of the body portion 26. The tip 30 is formed in a cylindrical shape, and a medicine discharge port 36 is opened at the distal end. The medicine discharge port 36 communicates with the medicine chamber 18 of the body portion 26 through a flow path 38 formed to extend in the axial direction inside the tip 30. In the flow path 38, a sealing portion 39 having an inner diameter smaller than that of the other portion and reduced in diameter is formed in the vicinity of the proximal end portion of the flow path 38.

The outer diameter of the tip 30 is reduced (i.e., outer diameter of the tip 30 decreases) in a tapered shape so as to gradually decrease from the proximal portion of the tip 30 toward the distal end portion of the tip 30, and can be fitted to a female Luer portion 302 (see FIG. 7) of another medical device 300 (for example, another syringe).

The Luer lock portion 32 protrudes shorter (i.e., less than) in the axial direction than the tip 30. A female screw portion 32a to which the cap 14 can be screwed is formed on an inner peripheral surface of the Luer lock portion 32.

The gasket 20 liquid-tightly seals the inside of the barrel body 12 and is slidably inserted in the axial direction, and sucks the diluent into the medicine chamber 18 at the time of mixing operation of the medicine 19 and the diluent in the medicine chamber 18. In addition, the gasket 20 sends out the medicine solution prepared in the medicine chamber 18 from the medicine discharge port 36. The distal end of the plunger 22 is connected to the gasket 20.

Figure 3:
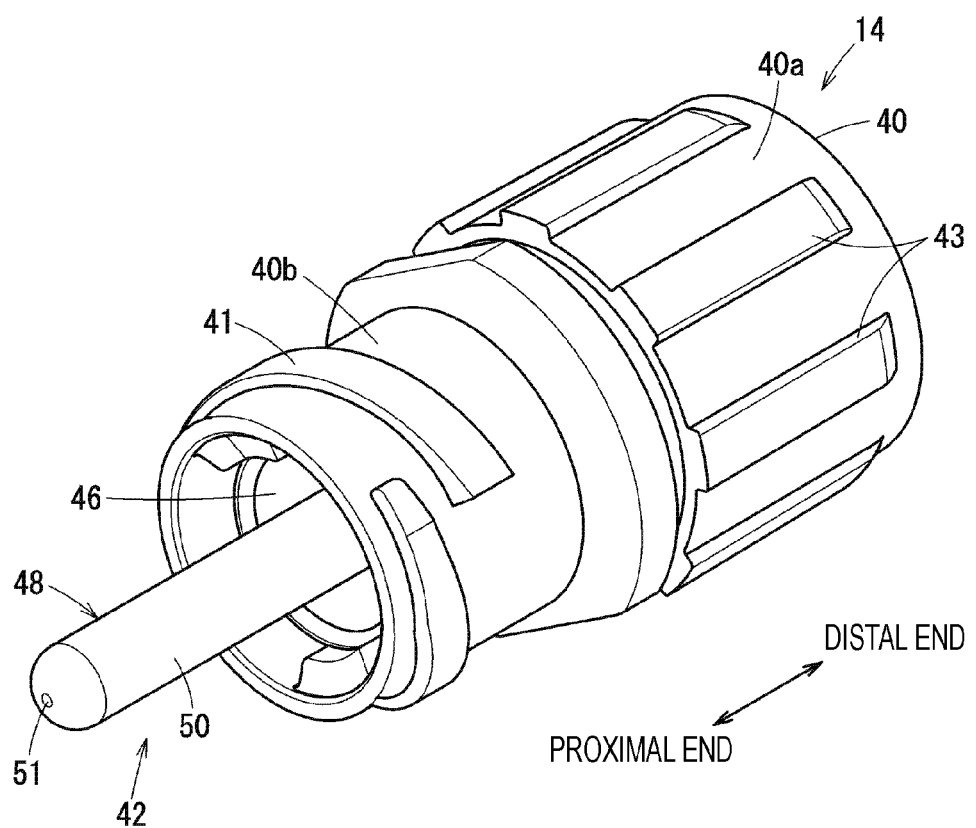
FIG. 3 is a perspective view of a cap of the prefilled syringe of FIG. 1.

As illustrated in FIG. 2, the cap 14 includes a cap body 40 screwed to the Luer lock portion 32 and a plug 42 supported by the cap body 40 to seal the medicine discharge port 36. As illustrated in FIG. 3, the cap body 40 is formed in a cylindrical shape, and the cap body 40 is provided with an operation portion 40a formed on the distal end side of the cap body 40 and a screw portion 40b formed on the proximal end side of the cap body 40. On the outer peripheral portion of the operation portion 40a, a plurality of anti-slip protrusions 43 arranged to be spaced apart in the circumferential direction are formed to extend in the axial direction. A male screw portion 41 that can be screwed into the female screw portion 32a of the Luer lock portion 32 is formed on an outer peripheral portion of the screwing portion 40b. As illustrated in FIG. 2, an attachment hole 44 penetrating in the axial direction is formed in the central portion of the cap body 40, and the plug 42 is attached to the attachment hole 44.

In accordance with an exemplary embodiment, the plug 42 can be made of an elastic material. The elastic material of the plug 42 can include, for example, rubber and a synthetic resin elastomer. Examples of the rubber of the plug 42 can include isoprene rubber, butyl rubber, latex rubber, and silicone rubber. As the synthetic resin elastomer of the plug 42, for example, a styrene elastomer, an olefin elastomer, or the like can be used.

The plug 42 is provided with an outer cylinder portion 46 that is in close contact (i.e., does not allow liquids or gases to pass through) with the outer peripheral portion of the tip 30 in a state where the cap 14 is attached to the tip 30, and a surface area increasing member 48 that is provided inside the outer cylinder portion 46 and inserted into the flow path 38. The surface area increasing member 48 of the present exemplary embodiment is provided as a cylindrical protrusion 50. In the vicinity of the base of the surface area increasing member 48, a base portion 49 having an inner diameter larger than the inner diameter of the medicine discharge port 36 is formed.

The base portion 49 is brought into close contact (i.e., does not allow liquids or gases to pass through) with the flow path 38, whereby the medicine discharge port 36 is liquid-tightly sealed. The protrusion 50 extends from the base portion 49 toward the proximal end side along the central axis with a constant diameter in the proximal end direction. The end 51 of the protrusion 50 extends to the proximal end side of the shoulder portion 28.

The diameter of the protrusion 50 is slightly smaller than the inner diameter of the medicine discharge port 36 and the diameter of the protrusion 50 is larger than the inner diameter of the sealing portion 39 of the flow path 38. In a state where the cap 14 is attached to the tip 30, the protrusion 50 and the sealing portion 39 are brought into close contact (i.e., does not allow liquids or gases to pass through) with each other, whereby the flow path 38 and the medicine chamber 18 are sealed. Therefore, the protrusion 50 help prevent the medicine 19 from flowing into the flow path 38. In addition, since a gap is formed between the protrusion 50 and the inner wall of the flow path 38 excluding the sealing portion 39, the protrusion 50 can be rather easily inserted into and removed from the flow path 38.

The proximal end side of the medicine chamber 18 is sealed with a gasket 20, and the front end side of the medicine chamber 18 is sealed with the plug 42 and the protrusion 50 of the medicine chamber 18. The volume of the medicine chamber 18 is larger than the occupied volume of the medicine 19. In a state where the medicine 19 is collected on the distal end side, a gap 18a is generated between the gasket 20 and the interface on the proximal end side of the medicine 19. An axial protrusion length L1 of the protrusion 50 into the medicine chamber 18 is longer than an axial length G of the gap 18a.

The medicine 19 can be solid, and is prepared into an injection solution by being dissolved in a diluent as described later immediately before use. In accordance with an exemplary embodiment, the medicine 19 can be a powdered powder or a porous lyophilizate obtained by freeze-drying the medicine substance in the medicine chamber 18. The medicine 19 may be solidified in a lump form or may be in a powder form. When the medicine 19 is solidified in a lump, as illustrated in FIG. 2, the protrusion 50 of the surface area increasing member 48 is solidified in a state of entering the lump of the medicine 19, and a recess 19a having a shape corresponding to the protrusion 50 is formed in the medicine 19. The surface area of the medicine 19 that can come into contact with the diluent increases by the recess 19a being formed in the medicine 19.

The prefilled syringe 10 of the present embodiment is configured as described above, and a manufacturing method of the prefilled syringe 10 will be described below.

Figure 4A:
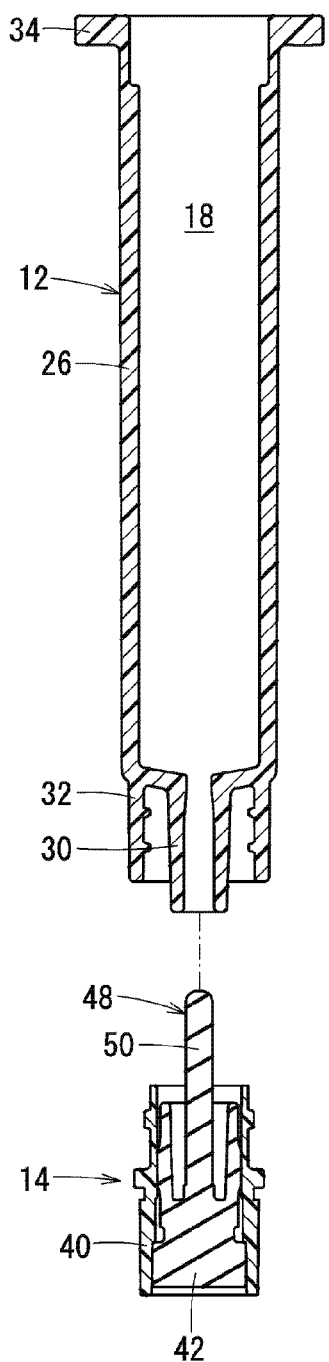
FIG. 4A is a cross-sectional view illustrating the method for manufacturing the prefilled syringe according to the first exemplary embodiment (part 1).

As illustrated in FIG. 4A, first, a user prepares the barrel body 12 and the cap 14. Then, the user attaches the cap 14 to the tip 30 and the Luer lock portion 32 of the barrel body 12.

Figure 4B:
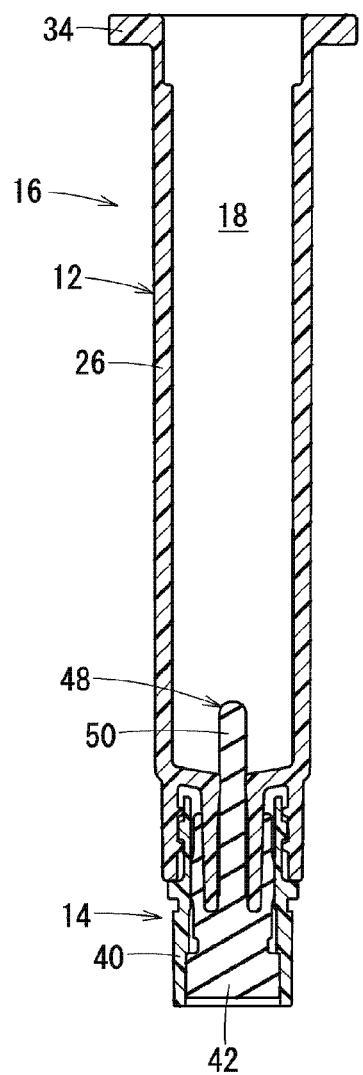
FIG. 4B is a cross-sectional view illustrating the method for manufacturing the prefilled syringe according to the first exemplary embodiment (part 2).

Through the above process, the syringe assembly 16 illustrated in FIG. 4B is completed. The syringe assembly 16 is stored and transported in a packaging container (tab) with the flange 34 disposed upward.

Figure 5A:
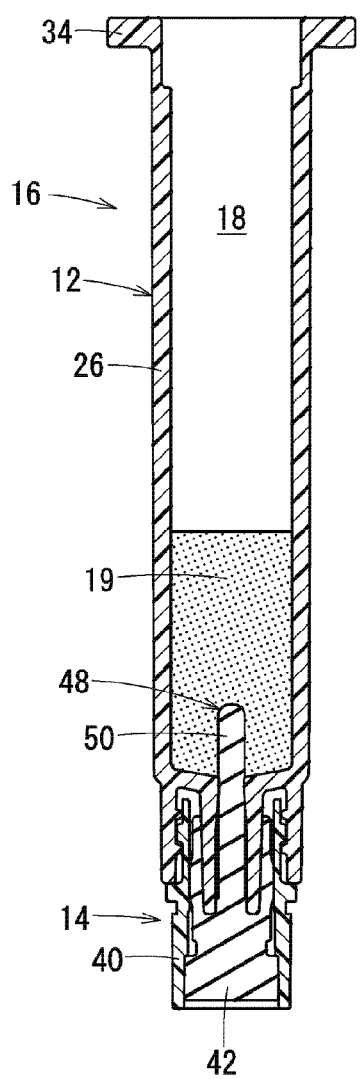
FIG. 5A is a cross-sectional view illustrating the method for manufacturing the prefilled syringe according to the first exemplary embodiment (part 3).

Thereafter, the syringe assembly 16 is carried into the medicine filling device, and is filled with the medicine 19 as illustrated in FIG. 5A. When the medicine 19 is a powder, the powder is charged into the medicine chamber 18 inside the barrel body 12 from the opening on the flange 34 side. When the medicine 19 is a lyophilizate, a solution containing the medicine 19 is injected into the medicine chamber 18, and the solution is frozen and dried under a reduced pressure environment. In the case of a lyophilizate, the medicine 19 is fixed so as to be fixed to the distal end side of the barrel body 12.

Figure 5B:
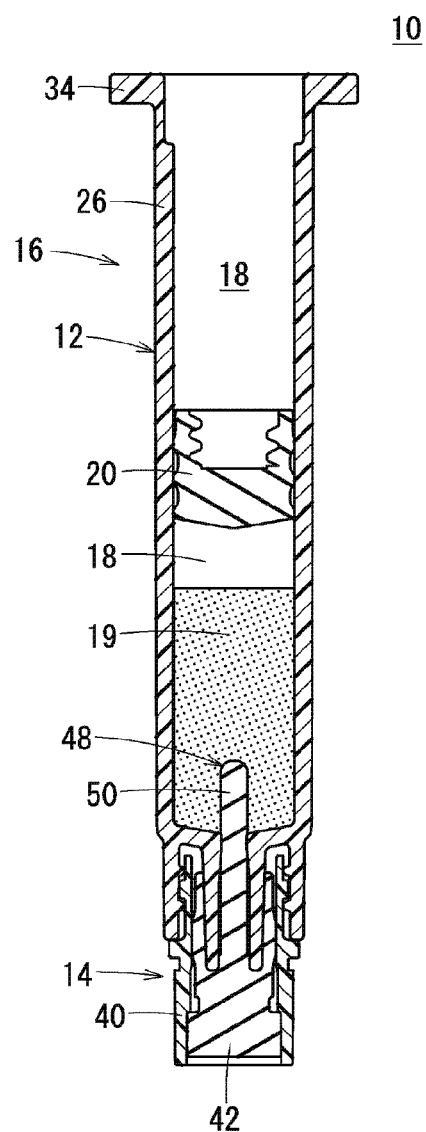
FIG. 5B is a cross-sectional view illustrating the method for manufacturing the prefilled syringe according to the first exemplary embodiment (part 4).

Thereafter, as illustrated in FIG. 5B, a plugging step of inserting the gasket 20 into the barrel body 12 is performed. In accordance with exemplary embodiment, the gasket 20 may be inserted under reduced pressure. Thereafter, the plunger 22 and the grip 24 (see FIG. 1) are attached to complete the prefilled syringe 10. In the prefilled syringe 10, the plunger 22 and the grip 24 may be attached as separate components immediately before use.

Next, the action of the prefilled syringe 10 of the present exemplary embodiment will be described together with a usage method.

Figure 6:
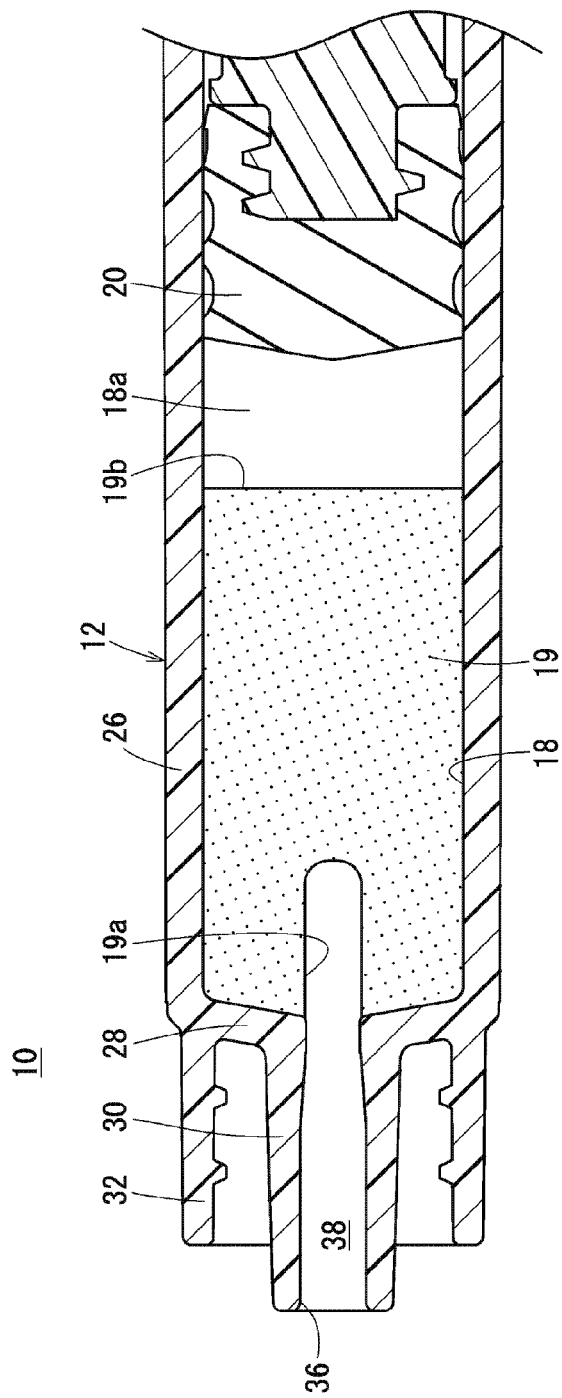
FIG. 6 is a cross-sectional view of a state in which a cap is removed from the prefilled syringe of FIG. 1.

As illustrated in FIG. 6, when using the prefilled syringe 10, the user removes the cap 14 from the barrel body 12. As a result, the surface area increasing member 48 (see FIG. 2) of the cap 14 is pulled out from the medicine 19 solidified in the lump, and the recess 19a having the shape corresponding to the protrusion 50 (FIG. 2) is exposed.

Figure 7:
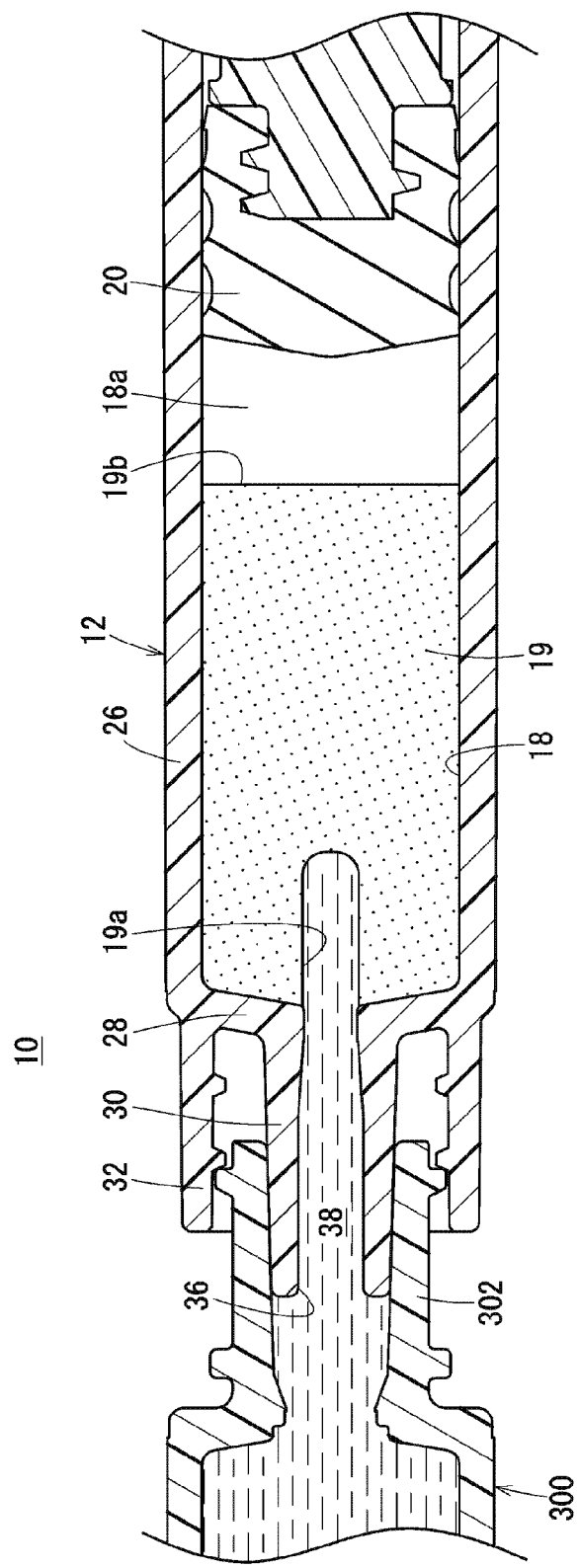
FIG. 7 is a cross-sectional view of a state in which a syringe for supplying a diluent is attached to the prefilled syringe of FIG. 1.

Next, as illustrated in FIG. 7, the user attaches the female Luer portion 302 of another medical device 300 (syringe) containing the diluent to the tip 30. Then, the user pushes a pusher on the medical device 300 side to send the diluent of the medical device 300 into the prefilled syringe 10.

The diluent of the medical device 300 flows into the medicine chamber 18 through the flow path 38 and comes into contact with the medicine 19 to dissolve the medicine 19. In the prefilled syringe 10 of the present embodiment, since the recess 19a is formed in the medicine 19, the area in which the medicine 19 comes into contact with the diluent increases, and thus the medicine 19 can be rather easily dissolved in the diluent.

Thereafter, the user removes the medical device 300 from the prefilled syringe 10, and attaches an injection needle to the tip 30 of the prefilled syringe 10 to be used.

In accordance with the present embodiment, the prefilled syringe 10 of the present embodiment includes: the barrel body 12 including the cylindrical body portion 26 having a medicine chamber 18 in which the medicine 19 is sealed, the shoulder portion 28 formed at the distal end of the body portion 26 and having a reduced diameter of the body portion 26, and the tip 30 extending from the distal end of the shoulder portion 28 toward the distal end side and having the flow path 38 formed in the tip 30; the gasket 20 inserted into the body portion 26 and sealing the proximal end side of the medicine chamber 18; and the cap 14 attached to the tip 30 and sealing the distal end side of the medicine chamber 18. The cap 14 includes the surface area increasing member 48 that extends toward the proximal end side, is inserted into the flow path 38 of the tip 30, and protrudes toward the medicine chamber 18 to increase a surface area of the medicine 19 solidified in a lump in the medicine chamber 18.

According to the prefilled syringe 10, since the surface area of the medicine 19 is increased by the surface area increasing member 48, the operation of dissolving the medicine 19 in the diluent can be rather easily performed.

In the prefilled syringe 10 described above, the surface area increasing member 48 may include the protrusion 50 protruding to a portion on the proximal end side of the shoulder portion 28. According to this configuration, since the recess 19a corresponding to the shape of the protrusion 50 is formed in the medicine 19, the surface area of the medicine 19 can be increased.

In the prefilled syringe 10, the axial protrusion length L1 of the protrusion 50 of the surface area increasing member 48 into the medicine chamber 18 may be longer than the axial length G of the gap 18a between the medicine 19 and the gasket 20. According to this configuration, since the surface area increasing member 48 can reliably pierce the medicine 19 when the medicine 19 is solidified, the surface area of the medicine 19 can be reliably increased.

In the prefilled syringe 10 described above, the medicine chamber 18 may seal the medicine 19 solidified in a lump, and the surface area increasing member 48 may form the recess 19a in the medicine 19 solidified in a lump. As a result, the diluent comes into contact with the recess 19a, and the medicine 19 can be rather quickly dissolved.

In the prefilled syringe 10, the lump-shaped medicine 19 may be fixed to the distal end side in the medicine chamber 18. According to this configuration, the surface area of the medicine 19 can be reliably increased by the surface area increasing member 48 protruding from the distal end side.

In the prefilled syringe 10, the medicine 19 may be a lyophilizate or a powder. According to this configuration, the lyophilizate or the powder that tends to be solidified in a lump can rather easily be dissolved with the diluent.

In the prefilled syringe 10, a gap may be formed between the outer peripheral portion of the surface area increasing member 48 and the inner peripheral surface of the flow path 38 of the tip 30. According to this configuration, the frictional resistance is reduced by reducing the contact area between the surface area increasing member 48 and the flow path 38, and insertion and removal of the surface area increasing member 48 into and from the flow path 38 can be rather easily performed.

In the prefilled syringe 10, the surface area increasing member 48 may be formed solid from a homogeneous material. According to this configuration, the structure of the surface area increasing member 48 can be simplified, and the moldability of the plug 42 can be improved.

In the prefilled syringe 10 described above, the cap 14 may include the cap body 40 connected to the barrel body 12 and the plug 42 supported by the cap body 40 to close the flow path 38 of the tip 30, and the surface area increasing member 48 may be formed to extend from the plug 42.

The syringe assembly 16 of the present exemplary embodiment includes: the barrel body 12 including the cylindrical body portion 26 having a medicine chamber 18 in which the medicine 19 is sealed, the tapered shoulder portion 28 formed at the distal end of the body portion 26 and having a reduced diameter of the body portion 26, and the tip 30 extending from the distal end of the shoulder portion 28 toward the distal end side and having the flow path 38 formed in the tip 30; and the cap 14 attached to the tip 30 and sealing the distal end side of the medicine chamber 18. The cap 14 includes the surface area increasing member 48 that extends toward the proximal end side, is inserted into the flow path 38 of the tip 30, and protrudes toward the medicine chamber 18 to increase a surface area of the medicine 19 solidified in a lump shape in the medicine chamber 18.

According to the syringe assembly 16, since the surface area of the medicine 19 solidified in a lump in the medicine chamber 18 can be increased, the operation of dissolving the medicine 19 with the diluent can be rather easily performed.

In the above-described method for manufacturing the prefilled syringe 10, the surface area increasing member 48 may protrude into the medicine chamber 18 before the medicine 19 in the medicine chamber 18 is solidified in a lump. As a result, the recess 19a can be formed in the medicine 19 solidified in a lump, and the surface area of the medicine 19 can be reliably increased.

Hereinafter, a modification of the cap 14 of the present exemplary embodiment will be described.

First Modification of Cap of First Exemplary Embodiment

Figure 8:
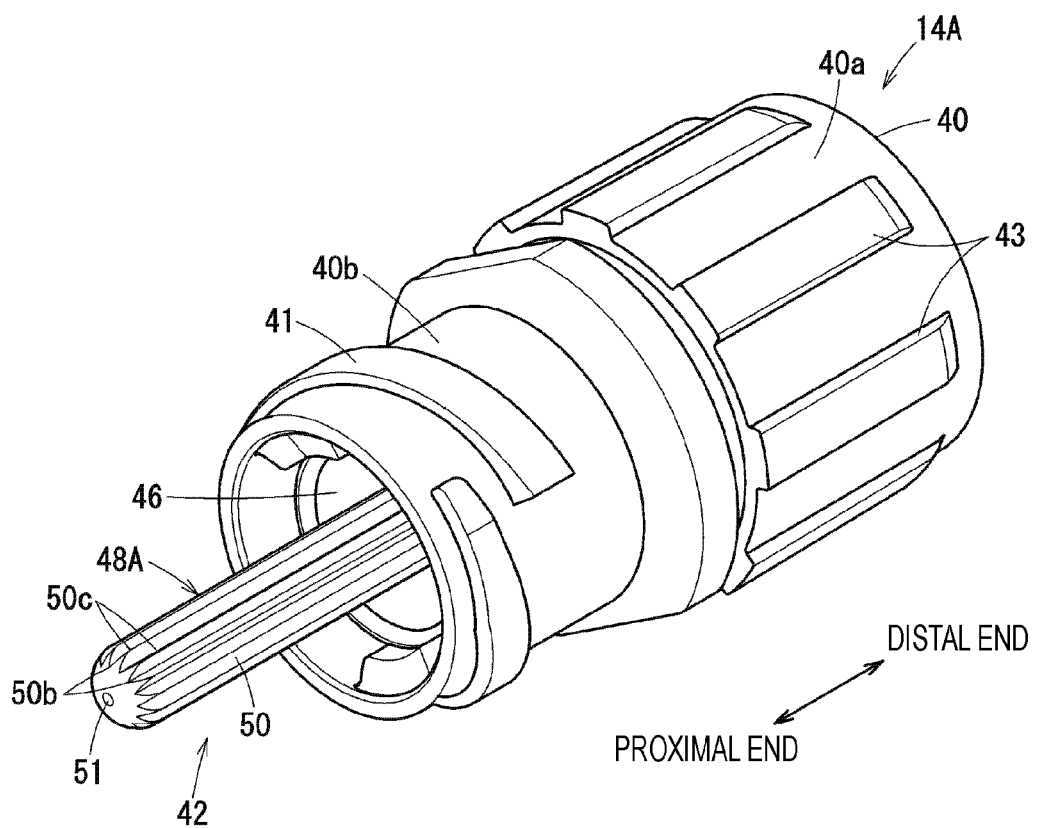
FIG. 8 is a perspective view illustrating a first modification of the cap.

As illustrated in FIG. 8, a cap 14A according to a first modification is different from the cap 14 of FIG. 3 in a surface area increasing member 48A. In the cap 14A, the same components as those of the cap 14 are denoted by the same reference numerals, and the detailed description of those components will be omitted.

In the surface area increasing member 48A of the present modification, a plurality of grooves 50b extending in the axial direction are provided at intervals in the circumferential direction on the outer peripheral portion of the protrusion 50. Fin-shaped ribs 50c are formed between the grooves 50b.

In the surface area increasing member 48A of the present modification, the rib 50c crushes the lump-shaped medicine 19 in accordance with the rotational operation with respect to the Luer lock portion 32 when the cap 14A is removed. As a result, the surface area of the medicine 19 can be increased, and the dissolution operation of the medicine 19 can be rather easily performed.

Second Modification of Cap of First Exemplary Embodiment

Figure 9:
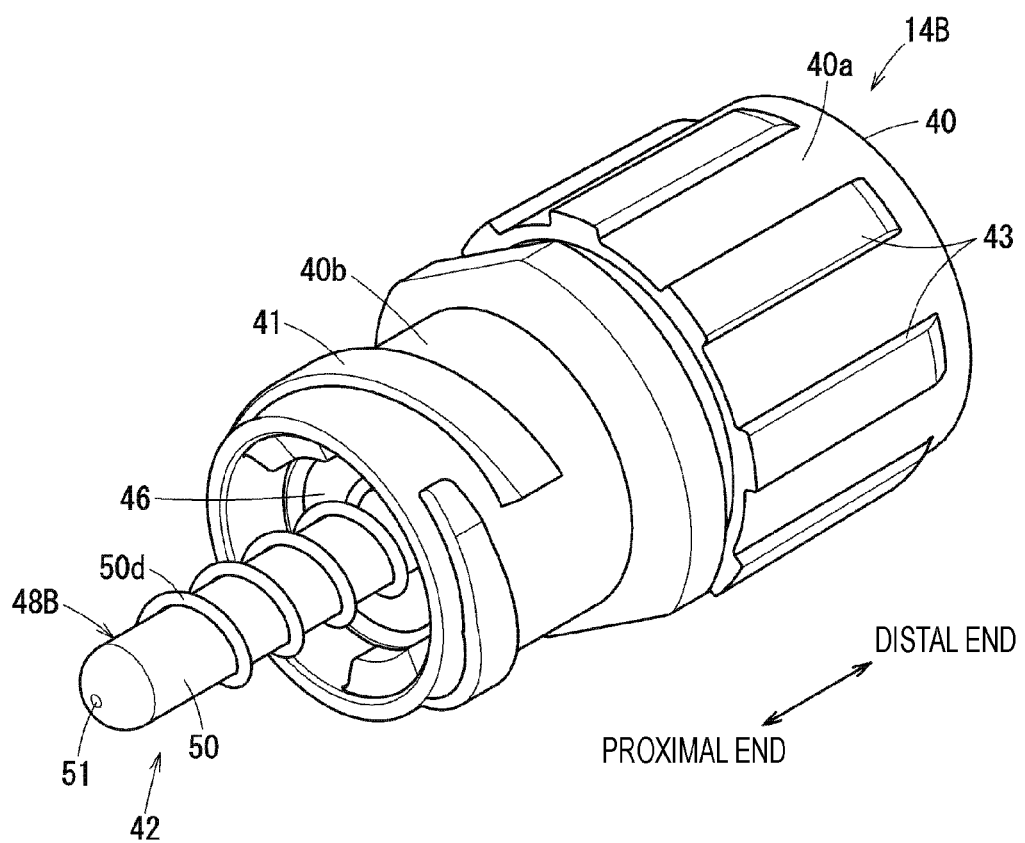
FIG. 9 is a perspective view illustrating a second modification of the cap.

As illustrated in FIG. 9, in a cap 14B according to a second modification, a spiral screw structure 50d is formed on the outer peripheral portion of the protrusion 50 constituting the surface area increasing member 48B. Also with the cap 14B of the present modification, the surface area of the medicine 19 solidified in a lump can be increased similarly to the cap 14A of the first modification.

Third Modification of Cap of First Exemplary Embodiment

Figure 10:
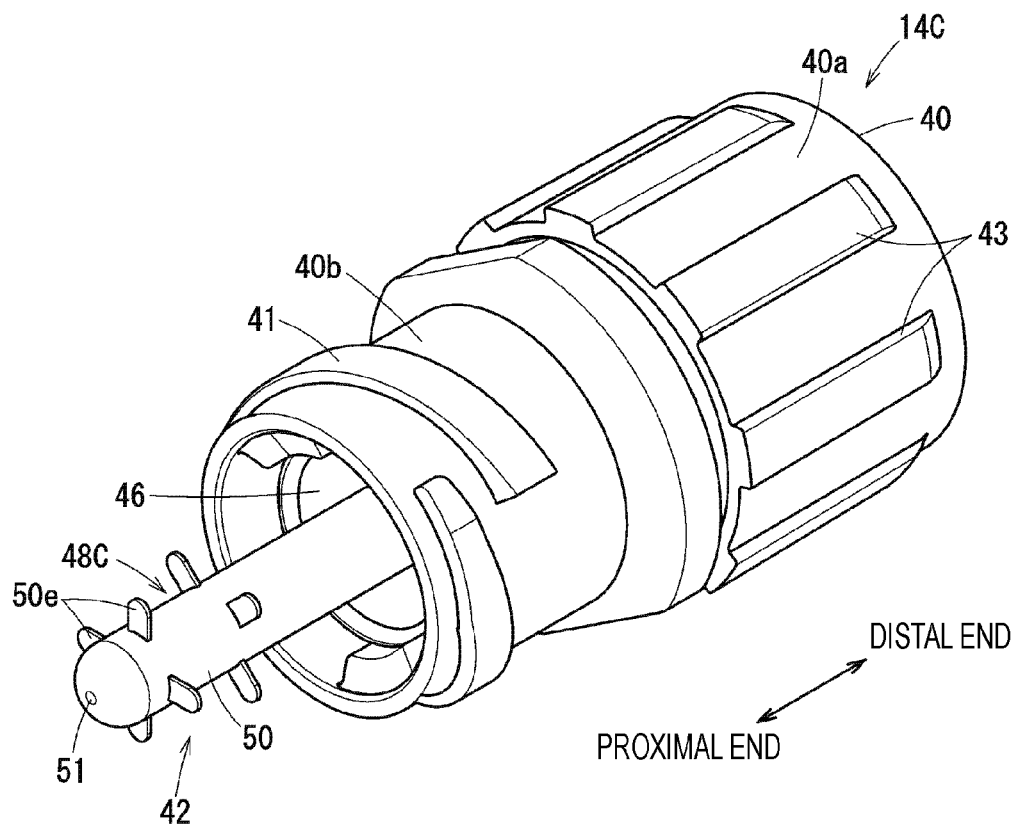
FIG. 10 is a perspective view illustrating a third modification of the cap.

As illustrated in FIG. 10, in a cap 14C according to a third modification, a convex portion 50e is provided on an outer peripheral portion of a protrusion 50 constituting a surface area increasing member 48C. In the surface area increasing member 48C of the present modification, the convex portion 50e crushes the lump-shaped medicine 19 in accordance with the rotational operation with respect to the Luer lock portion 32 when the cap 14C is removed. As a result, the surface area of the medicine 19 can be increased, and the dissolution operation of the medicine 19 can be rather easily performed.

Second Embodiment

Figure 11:
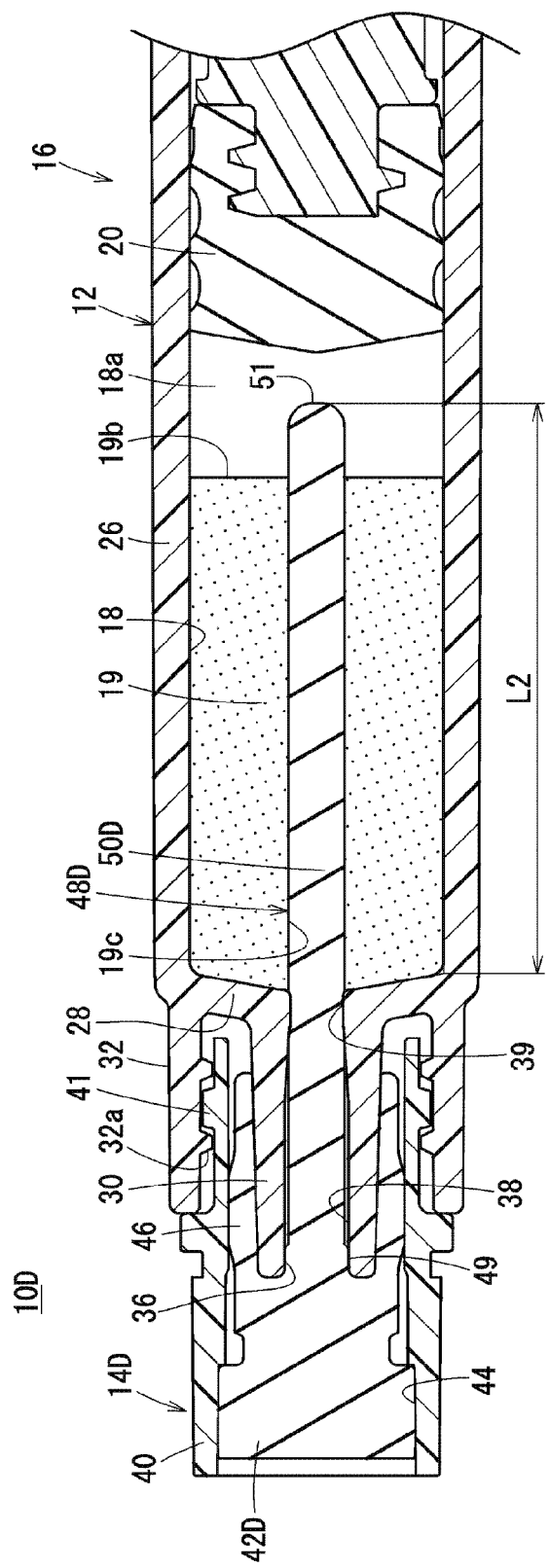
FIG. 11 is a cross-sectional view of the vicinity of a distal end of a prefilled syringe according to a second exemplary embodiment.

As illustrated in FIG. 11, a prefilled syringe 10D of the present embodiment is different from the prefilled syringe 10 described with reference to FIGS. 1 to 7 in a cap 14D. In the prefilled syringe 10D of the present embodiment, the same components as those of the prefilled syringe 10 of the first embodiment are denoted by the same reference numerals, and the detailed description of those components will be omitted.

As illustrated in FIG. 11, the prefilled syringe 10D is different from the prefilled syringe 10 of the first embodiment in the shape of the surface area increasing member 48D of the plug 42D of the cap 14D.

The surface area increasing member 48D includes a cylindrical protrusion 50D. A protrusion length L2 of the protrusion 50D into the medicine chamber 18 is set to be longer than a protrusion length L1 (see FIG. 2) of the protrusion 50 of the first embodiment. The end 51 of the protrusion 50D extends to the vicinity of the gasket 20. The protrusion 50D penetrates the lump-shaped medicine 19 in the axial direction, extends further to the proximal end side than a boundary 19b on the proximal end side of the lump-shaped medicine 19, and reaches the gap 18a between the proximal end side of the medicine 19 and the gasket 20.

In the present embodiment, the amount of the medicine 19 sealed in the medicine chamber 18 is set to such an amount that the position of the boundary 19b at the upper end of the medicine 19 does not reach the end 51 of the protrusion 50D when the prefilled syringe 10D is erected with the cap 14D facing downward. As a result, a through-hole 19c corresponding to the cross-sectional shape of the protrusion 50D is formed to penetrate the medicine 19 in the axial direction.

The prefilled syringe 10D of the present embodiment is similar to the prefilled syringe 10 of the first exemplary embodiment except for the sealed amounts of the cap 14D and the medicine 19, and can be manufactured by the method described with reference to FIGS. 4A to 5B.

Hereinafter, the operation of the prefilled syringe 10D of the present exemplary embodiment will be described.

Figure 12:
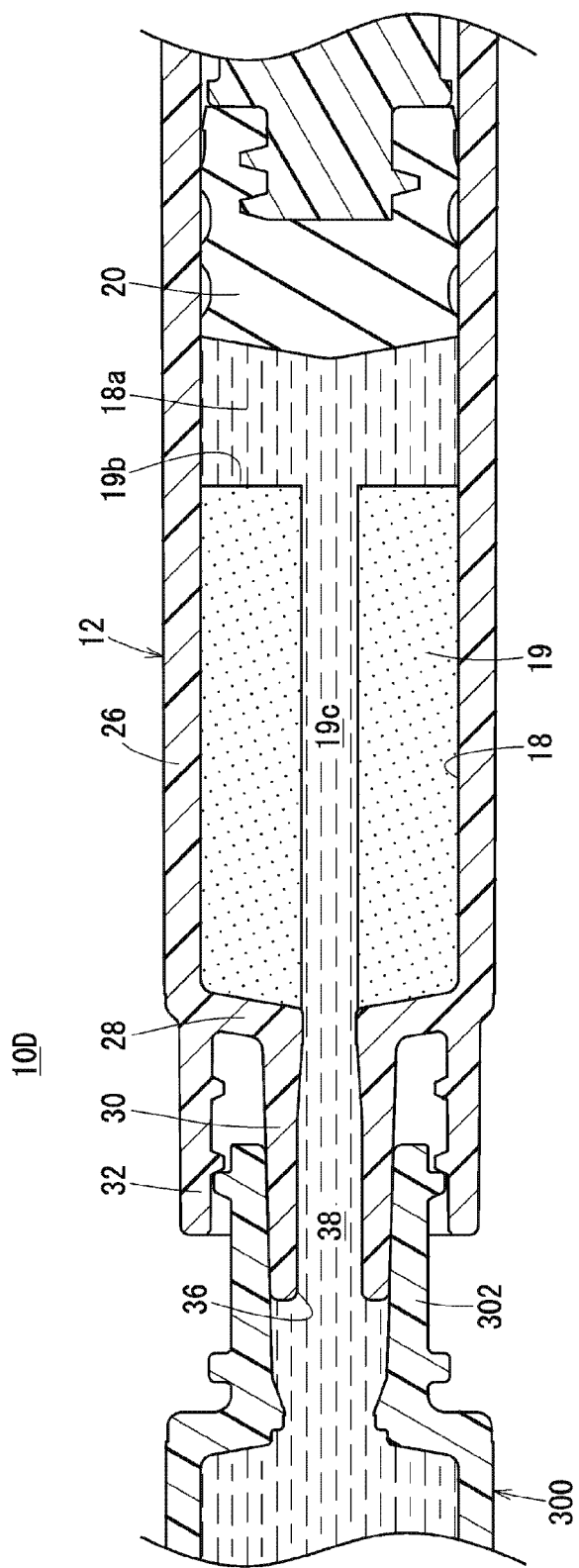
FIG. 12 is a cross-sectional view of a state in which a cap is removed from the prefilled syringe of FIG. 11.

As illustrated in FIG. 12, the cap 14D of the prefilled syringe 10D is removed immediately before use. Then, together with the cap 14D, the long protrusion 50D constituting the surface area increasing member 48D is pulled out from the medicine 19 in the medicine chamber 18. As a result, the through-hole 19c axially penetrating the medicine 19 appears. The flow path 38 of the tip 30 and the gap 18a of the medicine chamber 18 communicate with each other through the through-hole 19c.

Thereafter, the user connects the medical device 300 that supplies the diluent to the tip 30, and transfers the diluent from the medical device 300 to the medicine chamber 18. At this time, the diluent goes around to the gap 18a through the through-hole 19c. As a result, since the medicine 19 comes into contact with not only the portion of the through-hole 19c but also the diluent that has flown around to the gap 18a side, the contact area with the dissolved solution is increased, and the solubility of the dissolved solution can be increased.

In the prefilled syringe 10D of the present embodiment, the surface area increasing member 48D forms the through-hole 19c with respect to the medicine 19 solidified in a lump in the medicine chamber 18. As a result, the contact area between the solution and the medicine 19 can be further increased, and the solubility of the medicine 19 can be enhanced.

Third Exemplary Embodiment

Figure 13:
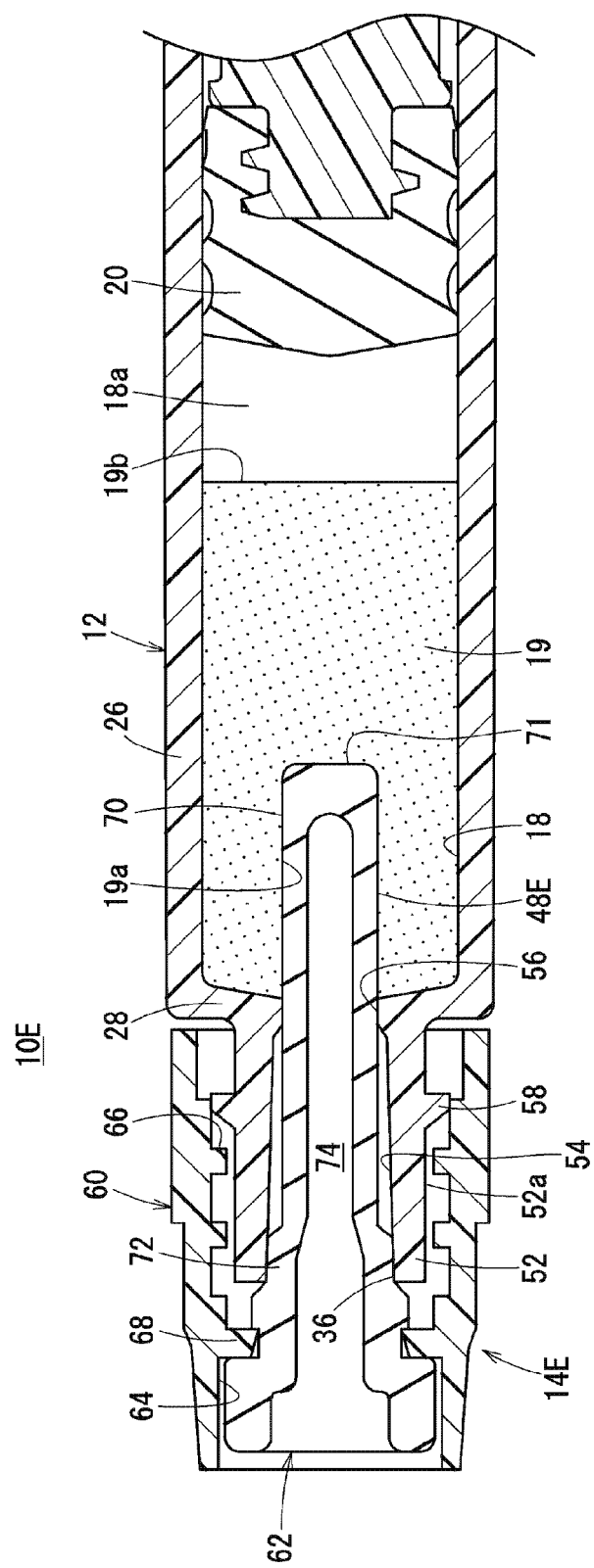
FIG. 13 is a cross-sectional view of the vicinity of a distal end of a prefilled syringe according to a third exemplary embodiment.

As illustrated in FIG. 13, in a prefilled syringe 10E of the present exemplary embodiment, a female tip 52 is provided at the distal end of the barrel body 12, and a cap 14E also has a shape that can be attached to the tip 52. In the prefilled syringe 10E of the present exemplary embodiment, the same components as those of the prefilled syringe 10 described with reference to FIGS. 1 to 7 are denoted by the same reference numerals, and a detailed description of those component will be omitted.

The tip 52 (female Luer portion) has a shape that can be connected to a male tip of a medical device (not illustrated) that supplies a diluent, and an accommodation hole 54 that can accommodate the male tip is formed to extend in the axial direction. The accommodation hole 54 is formed in a tapered shape in which the inner diameter of the accommodation hole 54 becomes slightly smaller from the distal end side toward the proximal end side. A reduced diameter portion 56 whose diameter is reduced inward (i.e., decreases inward) is formed on the proximal end side of the accommodation hole 54. The reduced diameter portion 56 is in close contact (i.e., does not allow liquids or gases to pass through) with a protrusion 70 of the cap 14E described later to partition the medicine chamber 18 and the accommodation hole 54, and prevent leakage of the medicine 19 to the accommodation hole 54. The tip 52 extends in the axial direction with a constant outer diameter 52a, and a male screw 58 to which the cap 14E is screwed is formed at a predetermined portion of the outer peripheral portion.

The cap 14E is connected to the tip 52. The cap 14E includes a cap body portion 60 screwed and connected to the tip 52 and a plug 62 inserted into the accommodation hole 54 of the tip 52 to close the accommodation hole 54. The cap body portion 60 is a cylindrical member having an attachment hole 64 having an inner diameter larger than the outer diameter 52a of the tip 52. A female screw 66 screwed to the male screw 58 of the tip 52 is formed on the inner peripheral surface on the proximal end side of the attachment hole 64 of the cap body portion 60. The plug 62 is provided inside the attachment hole 64. The plug 62 is supported by the cap body portion 60 by being engaged with a rib 68 protruding inward from the attachment hole 64 of the cap body portion 60.

The plug 62 has a surface area increasing member 48E extending from the engaging portion with the rib 68 to the proximal end side. The surface area increasing member 48E has a protrusion 70 protruding into the medicine chamber 18 and a base portion 72 adjacent to the rib 68. The base portion 72 has an outer diameter in close contact (i.e., does not allow liquids or gases to pass through) with the medicine discharge port 36 in the vicinity of the distal end of the accommodation hole 54 of the tip 52, and seals the medicine discharge port 36. The protrusion 70 is a portion further extending from the base portion 72 toward the proximal end side, and is formed to have an outer diameter smaller than that of the base portion 72. The protrusion 70 is in close contact (i.e., does not allow liquids or gases to pass through) with the reduced diameter portion 56 at the boundary portion between the medicine chamber 18 and the accommodation hole 54. The outer diameter of the protrusion 70 is smaller than the inner diameter of the accommodation hole 54 in a portion other than the reduced diameter portion 56, and a gap is formed between the protrusion 70 and the inner peripheral surface of the accommodation hole 54.

As illustrated in the FIG. 13, the protrusion 70 protrudes to the medicine chamber 18, and forms the recess 19a in the medicine 19 solidified in a lump shape. Note that the length of the protrusion 70 is not limited to the illustrated example, and may be formed to have a length that penetrates the medicine 19 in the axial direction.

In addition, a hollow portion 74 extending in the axial direction is formed in the central portion of the plug 62. The hollow portion 74 opens on the distal end side and extends to the vicinity of an end portion 71 of the protrusion 70 on the proximal end side. The protrusion 70 is formed in a cylindrical shape by the hollow portion 74 so as to exhibit appropriate elasticity.

Figure 14:
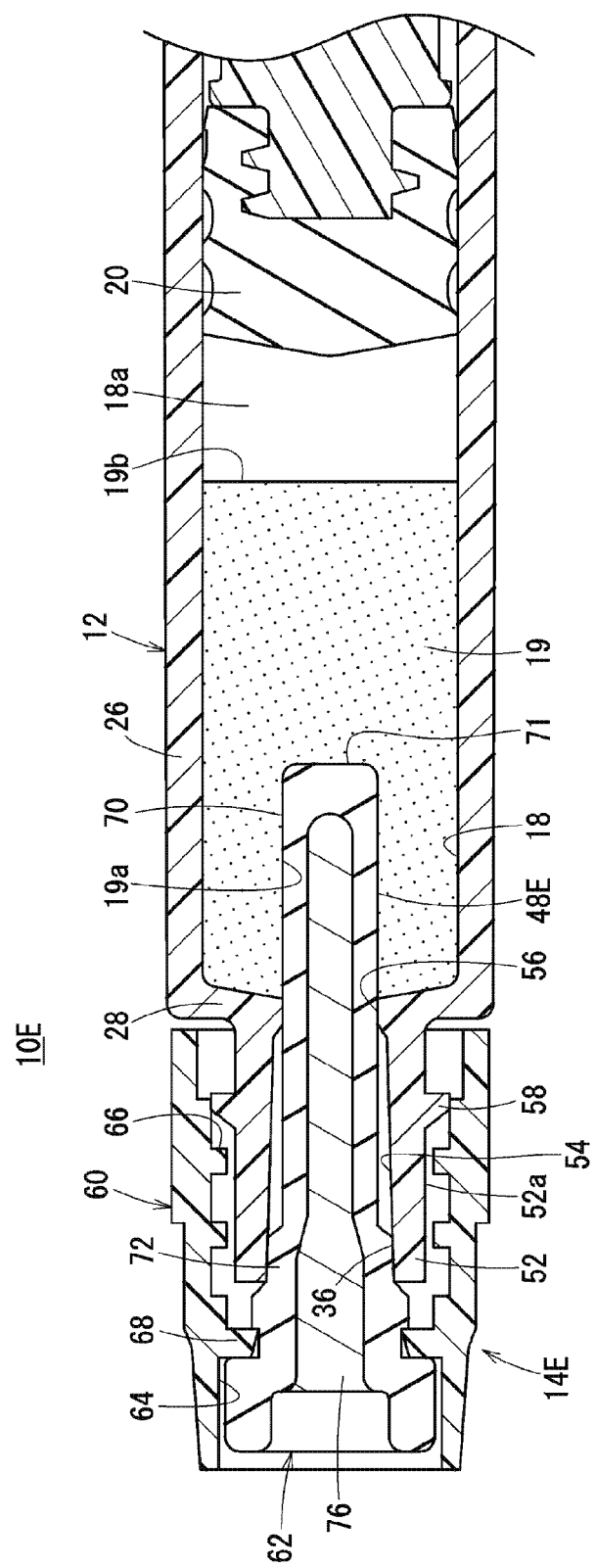
FIG. 14 is a cross-sectional view of the vicinity of a distal end of a prefilled syringe according to a fourth exemplary embodiment.

Note that the hollow portion 74 may not be formed in the plug 62. As illustrated in FIG. 14, a core member 76 made of a relatively hard material may be inserted into the plug 62. In a case where the protrusion 70 is formed to be long and the medicine 19 penetrates in the axial direction, it is preferable to provide the core material 76 because deformation of the protrusion 70 can be prevented.

The detailed description above describes embodiments of a prefilled syringe provided by enclosing a powdery medicine in the prefilled syringe, a syringe assembly, a method for manufacturing a prefilled syringe, and a method for increasing a surface area of a medicine solidified in a lump in a prefilled syringe. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A prefilled syringe comprising:
a barrel body including a cylindrical body portion having a medicine chamber in which a medicine is sealed, a shoulder portion formed at a distal end of the body portion and having a reduced diameter of the body portion, and a tip extending from a distal end of the shoulder portion toward a distal end side and having a flow path formed in the tip;
a gasket configured to be inserted into the body portion and to seal a proximal end side of the medicine chamber;
a cap configured to be attached to the tip and to seal a distal end side of the medicine chamber, wherein the cap includes a surface area increasing member that extends toward a proximal end side and configured to be inserted into the flow path of the tip, and protrudes toward the medicine chamber to increase a surface area of the medicine that has been solidified in a lump in the medicine chamber;
the surface area increasing member being configured to penetrate the solidified medicine in an axial direction, and when the cap is removed from the tip, the flow path of the tip is configured to communicate with a gap of the medicine chamber on the proximal end side of the solidified medicine; and
wherein the surface area increasing member is configured to extend further to the proximal end side than a boundary on the proximal end side of the solidified medicine, and a through-hole axially penetrating the solidified medicine appears when the cap is removed from the tip, and the flow path of the tip is configured to communicate with the gap of the medicine chamber through the through-hole.

2. The prefilled syringe according to claim 1, wherein the surface area increasing member includes a protrusion protruding to a portion on a proximal end side of the shoulder portion.

3. The prefilled syringe according to claim 1, wherein an axial protrusion length of the surface area increasing member into the medicine chamber is longer than an axial length of a gap between the medicine and the gasket.

4. The prefilled syringe according to claim 3, wherein the medicine chamber is configured to seal the solidified medicine.

5. The prefilled syringe according to claim 4, wherein the solidified medicine is fixed to a distal end side in the medicine chamber.

6. The prefilled syringe according to claim 1, wherein the medicine is a lyophilizate or a powder.

7. The prefilled syringe according to claim 1, wherein a gap is formed between an outer peripheral portion of the surface area increasing member and an inner peripheral surface of a flow path of the tip.

8. The prefilled syringe according to claim 1, wherein the surface area increasing member includes a hollow portion in a central portion of the surface area increasing member.

9. The prefilled syringe according to claim 1, wherein the surface area increasing member includes a material having a hard core in the surface area increasing member.

10. The prefilled syringe according to claim 1, wherein the surface area increasing member is formed of a solid homogeneous material.

11. The prefilled syringe according to claim 1, wherein:
the cap includes a cap body connected to the barrel body;
a plug that is supported by the cap body and closes the flow path of the tip; and
the surface area increasing member extends from a body of the plug.

12. A method for manufacturing the prefilled syringe according to claim 1, comprising:
causing the surface area increasing member to protrude into the medicine chamber before the medicine in the medicine chamber is solidified into a lump.

13. A surface area increasing method for increasing the surface area of the medicine solidified in the lump in the medicine chamber using the prefilled syringe according to claim 1, the method comprising:
increasing the surface area of the medicine by relatively moving the surface area increasing member protruding to the medicine chamber with respect to the medicine when removing the cap.

14. A syringe assembly comprising:
a barrel body including a cylindrical body portion having a medicine chamber configured to receive a medicine, a shoulder portion formed at a distal end of the body portion and having a reduced diameter of the body portion in a tapered shape, and a tip extending from a distal end of the shoulder portion toward a distal end side and having a flow path formed in the tip; and
a cap configured to be attached to the tip and to seal a distal end side of the medicine chamber, wherein the cap includes a surface area increasing member that extends toward a proximal end side and is inserted into the flow path of the tip, and protrudes toward the medicine chamber to increase a surface area of the medicine that has been solidified in the medicine chamber;

the surface area increasing member being configured to penetrate the solidified medicine in an axial direction, and when the cap is removed from the tip, the flow path of the tip is configured to communicate with a gap of the medicine chamber on the proximal end side of the solidified medicine; and wherein the surface area increasing member is configured to extend further to the proximal end side than a boundary on the proximal end side of the solidified medicine, and a through-hole axially penetrating the solidified medicine appears when the cap is removed from the tip, and the flow path of the tip is configured to communicate with the gap of the medicine chamber through the through-hole.

15. The syringe assembly according to claim 14, wherein the surface area increasing member includes a protrusion protruding to a portion on a proximal end side of the shoulder portion.

16. The syringe assembly according to claim 14, wherein the medicine chamber is configured to seal the solidified medicine.

17. The syringe assembly according to claim 14, wherein:
the cap includes a cap body connected to the barrel body;
a plug that is supported by the cap body and closes the flow path of the tip; and
the surface area increasing member extends from a body of the plug.

18. A syringe assembly comprising:
a barrel body including a cylindrical body portion includes a medicine chamber configured to receive a medicine, a shoulder portion formed at a distal end of the body portion and having a reduced diameter of the body portion, and a tip extending from a distal end of the shoulder portion toward a distal end side and having a flow path formed in the tip;

a gasket configured to be inserted into the body portion and to seal a proximal end side of the medicine chamber; and a cap configured to be attached to the tip and to seal a distal end side of the medicine chamber, wherein the cap includes a surface area increasing member that extends toward a proximal end side and configured to inserted into the flow path of the tip, and protrudes toward the medicine chamber to increase a surface area of the medicine that has been solidified in the medicine chamber;

the surface area increasing member being configured to penetrate the solidified medicine in an axial direction, and when the cap is removed from the tip, the flow path of the tip is configured to communicate with a gap of the medicine chamber on the proximal end side of the solidified medicine; and wherein the surface area increasing member is configured to extend further to the proximal end side than a boundary on the proximal end side of the solidified medicine, and a through-hole axially penetrating the solidified medicine appears when the cap is removed from the tip, and the flow path of the tip is configured to communicate with the gap of the medicine chamber through the through-hole.

19. The syringe assembly according to claim 18, wherein the surface area increasing member includes a protrusion protruding to a portion on a proximal end side of the shoulder portion.

* * * * *